United States Patent [19]

Fey et al.

[11] Patent Number: 4,720,372
[45] Date of Patent: Jan. 19, 1988

[54] DEVICE FOR THE EVALUATION OF A FLAT TEST CARRIER FOR THE ANALYTICAL DETERMINATION OF COMPONENTS OF BODY FLUIDS

[75] Inventors: Werner Fey, Pfungstadt; Manfred Pauli, Schwetzingen; Uwe Ruppender; Manfred Seidenstricker, both of Mannheim, all of Fed. Rep. of Germany

[73] Assignee: Boehringer Mannheim GmbH, Mannheim, Fed. Rep. of Germany

[21] Appl. No.: 619,017

[22] Filed: Jun. 11, 1984

[30] Foreign Application Priority Data

Jun. 16, 1983 [DE] Fed. Rep. of Germany ....... 3321783

[51] Int. Cl.$^4$ ...................... G01N 21/00; G01N 21/13
[52] U.S. Cl. ........................................ 422/67; 422/63; 422/68
[58] Field of Search .................. 422/63, 64, 66, 68, 422/67; 436/46, 50; 219/543, 499, 449, 464, 504

[56] References Cited

U.S. PATENT DOCUMENTS

| 2,533,286 | 12/1950 | Schmitt | 219/499 |
|---|---|---|---|
| 2,918,558 | 12/1959 | Evans | 219/499 |
| 4,011,048 | 3/1977 | Johnson, Jr. et al. | 422/63 |
| 4,038,030 | 7/1977 | Albright et al. | |
| 4,059,405 | 11/1977 | Sodickson et al. | 422/68 |
| 4,296,069 | 10/1981 | Smith et al. | 422/64 |
| 4,303,611 | 12/1981 | Jessop | |
| 4,356,379 | 10/1982 | Groeme | 219/121 LJ |
| 4,430,299 | 2/1984 | Horne | 436/48 |
| 4,468,963 | 9/1984 | Schauble | 73/204 |
| 4,488,810 | 12/1984 | Hatanaka et al. | 422/64 |
| 4,527,050 | 7/1985 | Kicherer | 219/464 |

FOREIGN PATENT DOCUMENTS 75766 9/1982 European Pat. Off. .

Primary Examiner—David L. Lacey
Assistant Examiner—C. M. Delahunty
Attorney, Agent, or Firm—Felfe & Lynch

[57] ABSTRACT

The present invention provides a device for the evaluation of a flat test carrier for the analytical determination of components of body fluids, said device having a tempering device and a regulating unit, the tempering device including a heating and measurement unit which can be pressed flatly against the test carrier in the region of its reference surface utilized for the evaluation and having a heating surface, wherein the heating and measurement unit has a heating surface which can be homogeneously heated with at least one resistance heating element, at least one resistance heating element is associated at least partly in close proximity to the heating surface, at least one part, serving as temperature measurement section, of the part of the resistance heating element arranged in the neighborhood of the heating surface consisting of a material with a temperature-dependent electrical resistance and the electrical resistance of the temperature measurement section is used for the regulation of the temperature of the heating and measurement unit by means of the regulating unit so that a part of the heating element simultaneously serves as temperature measurement element.

8 Claims, 7 Drawing Figures

DEVICE FOR THE EVALUATION OF A FLAT TEST CARRIER FOR THE ANALYTICAL DETERMINATION OF COMPONENTS OF BODY FLUIDS

The present invention is concerned with a device for the evaluation of a flat test carrier for the analytical determination of components of body fluids, said device having a tempering device and a regulating unit, the tempering device including a heating and measurement unit which can be pressed flatly on the test carrier in the region of its test surface utilised for the evaluation.

Besides the well-known methods of analysis for the quantitative determination of components of blood or urine, in which liquid reagents are used, in clinical chemistry the use of solid test carriers has achieved increasing importance. These are often formed as flat sheets or longitudinal bodies in the manner of test strips long since known especially for qualitative investigations. They can be handled especially easily even by persons with little training and can be evaluated with comparatively simply constructed and, therefore, inexpensive apparatus.

A central problem in the evaluation of such test carriers is the tempering thereof. In the case of the conventional enzymatic determinations, even very small temperature variations can already influence the exactitude of the analysis to a considerable extent. Therefore, it must be an aim to maintain the predetermined analysis temperature, for example 37° C., with a very high degree of exactitude of about 0.1° C.

In principle, a flat object, for example, the above-mentioned test carrier, can be tempered very accurately if, in the region of the area thereof used for the evaluation, it is brought into contact with appropriate heating surfaces which can be brought to a definite temperature by means of heating elements, for example resistance heating wires, measurement elements, for example thermo-elements, and an associated regulating unit. Such a device is described, for example, in U.S. Pat. No. 4,038,030.

However, a sufficiently rapid and thus economic evaluation of the test carrier leads to high requirements which cannot be sufficiently fulfilled with the previously known tempering devices. Thus, in particular, a very rapid achievement of the measurement temperature is to be aimed for. In the case of an experimentally tested embodimental example of the present invention, for example, the end temperature is achieved in about 40 seconds. Advances in the development of appropriate test carriers further resulted in that, with the object of reducing the amounts of samples and reagents, ever smaller surfaces are available for the evaluation. Thus, the surface of the test field of a test carrier made, for example, as a test strip is only 6 mm.× 6 mm. Of this, for various reasons, only a circle of about 4 mm. diameter can be used for the evaluation, which is usually carried out as a photometric determination of the diffuse reflection ability. Finally, the appropriate evaluation apparatus should, as far as possible, be available decentrally in every medical practice and it is, therefore, important that the device for tempering can also be constructed economically.

Therefore, it is an object of the present invention to provide a device for homogeneously and precisely tempering a small reference surface of a test carrier in a very short period of time.

Thus, according to the present invention, there is provided a device for the evaluation of a flat test carrier for the analytical determination of components of body fluids, said device having a tempering device and a regulating unit, the tempering device including a heating and measurement unit which can be pressed flatly against the test carrier in the region of its test surface utilised for the evaluation and having a heating surface, wherein the heating and measurement unit has a heating surface which can be homogeneously heated with at least one resistance heating element. At least one resistance heating element is associated at least partly in close proximity to the heating surface, at least one portion, serving as temperature measurement section, of the part of the resistance heating element arranged in the neighbourhood of the heating surface consisting of a material with a temperature-dependent electrical resistance and the electrical resistance of the temperature measurement section is used for the regulation of the temperature of the heating and measurement unit by means of the regulating unit so that that portion of the heating element simultaneously serves as a temperature measuring and a heating element.

The mentioned temperature measurement section arranged in close proximity to the heating surface of the heating and measurement unit thus forms a combined heating and temperature measurement element. This is of considerable advantage in the case of the homogeneous tempering of a very small surface. Thus, if a separate temperature measurement element were used and were this arranged very close to the tempering surface, as is desirable for a good regulation, then it would be impossible also to heat at the same place. Admittedly, the inhomogeneity thereby produced could be avoided by providing a sufficiently thick, good heat-conducting layer, for example of copper, for the temperature compensation. However, such a heating and measurement unit would have a very high heat capacity which, in turn, is disadvantageous for a rapid regulating behaviour. Furthermore, in the case of the solution to the problem according to the present invention, the distances present in the case of separate heating and measurement elements do not arise, with the result that very small regulation time constants are achieved.

As resistance heating element, there can be used, for example, an insulatdly mounted resistance wire in an appropriate construction part made by metal injection moulding. The injection moulded part can have, on one side, a smooth surface as heating surface for pressing on to the test carrier and, on the other side, a corresponding profiling for the heating wires. A section of the heating wires arranged in the proximity of the smooth surface, which, in contradistinction to the usually preferred heating wires, consists of a material with temperature-dependent resistance, is arranged in the proximity of the smooth heating surface and provided with appropriate electrical tappings via which the electric resistance can be determined and can be used for temperature measurement or temperature regulation.

However, such a construction is very laborious. Therefore, for the heating and measurement unit, there is especially preferred a flat substrate and especially a ceramic plate. The substrate has, on the side facing the test carrier, either a smooth surface which directly forms the heating surface in contact with the test carrier or, according to a preferred embodiment of the present invention, it is full-facedly connected with a metal plate, the surface of which remote from the ceramic substrate for its part forms the preferably smoothly formed heating surface.

On the substrate are present resistance strips which are used as heating element or elements and at least a part of which is tapped off by appropriate lead-off wires and thus forms the temperature measurement section. The resistance strips are preferably vapour deposited on a ceramic plate with a thickness of at most 2 mm. and especially preferably of less than 1 mm. The metal with a temperature-dependent resistance can be, for example, platinum.

This preferred construction is especially economic to produce. Ceramic platelets with vapour-deposited platinum layers are produced on a large scale as measurement resistances. They contain homogeneously distributed resistance strips arranged very close to one another, for example in the form of a meandering pattern. It is also not a problem to contact such platinum strips with appropriate wires at various positions or also to interrupt the strips so that certain parts can be individually heated by the passage of current or used individually for the measurement.

Due to the small thickness of the ceramic substrate, there is provided a close thermal coupling between the resistance strips and the heating surface in contact with the test carrier. Furthermore, the small mass results in very small delays in the regulation behaviour and thus in a very rapid thermosetting. In spite of the small heat capacity, because of the uniform heating which is not interrupted by a separate measurement sensor, there is achieved an outstanding homogeneity, even in the case of tempering extremely small surfaces.

The mentioned laminated construction, in which the substrate carrying the resistance strips is full-facedly connected with a metal surface, combines the mentioned advantages of the ceramic substrate with the advantages of a metal plate carrying the contact surface, namely, an additional heat compensation and the production-technical advantages of metallic in comparison with ceramic constructional parts.

In order to achieve the smallest possible backwards conducting away of heat from the resistance strips, i.e. away from the substrate carrying them, the heating and measurement unit is preferably so constructed that, behind the substrate there is provided a hollow chamber enclosing the resistance strips, which hollow chamber acts thermally insulatingly.

In an especially preferred embodiment, there are present at least two temperature measurement sections in immediate proximity to the heating surface. These, together with two reference resistances, are connected into a measurement bridge. In the case of each measurement section, one measurement resistance lies on an input of the measurement bridge. The measurement bridge is powered either with a constant voltage or, according to an especially preferred embodiment, with the feed voltage, controlled by the regulating unit, for the production of electrical heating power. The reference resistances preferably have a constant resistance value which corresponds to the resistance value of the associated combined heating and measurement resistance in the case of the desired actual temperature, for example 37° C. The voltage across the bridge diagonals, which represents a measure for the actual temperature value, becomes zero, in this case, independently of the feed voltage of the bridge, in the case of achievement of the desired temperature. It is thereby possible that the combined heating and measurement elements simultaneously heat with a direct current and are used for the temperature measurement. Furthermore, the circuit-technical expense is very low. However, other circuits are also possible in which the combined heating and measurement resistances are used alternatingly for temperature measurement and for heating. This can be especially desirable in the case of the use of digital electronic means for the regulation.

In an important embodiment, after the insertion and/or laying on of the test carrier, an increased heating power can be applied to the test carrier. A rapid heating up of the test carrier to the required temperature is achieved, the particular heating power applied thereby being correspondingly provided for the particular requirements and ancillary conditions. The increased heating capacity is, according to the present invention, achieved with dependence upon the energy removed in the case of laying a test carrier on the heating and measurement unit. For this purpose, the energy given up from the heating and measurement unit to the test carrier is integrated up and a corresponding correction signal is introduced to the temperature desired value, which is supplied to the regulator.

In order to be able to carry out the explained desired value correction with a small circuit-technical expenditure, after the integrating up, an integration condenser present in the integrator is discharged, a time constant thereby being presupposed. A corresponding discharge signal is then passed to the regulator for the correction. A rapid heating up of the test carrier is guaranteed. The controlling of the integrator and also the discharging takes place with the help of a processor.

In order to keep the influence of the surrounding temperature or of the inner temperature of the device on the measurement result as small as possible, in a preferred embodiment, there is provided a measurement device for the apparatus inner temperature in order to pass a corresponding correction value to the regulator. As already mentioned above, between the measurement place, at which the measurement element or elements is or are arranged, and the test place in the test field, an unavoidable distance is present even in the case of the construction according to the present invention. Since heat continuously flows off from the test field to the cooler surroundings (in the case of a test strip, especially through the base strip consisting of synthetic resin). between the test place and the measurement place there exists a temperature difference which is dependent upon the surrounding temperature. With the measurement device, there is produced a correction value which acts upon the regulator. This measurement device preferably also contains a measurement bridge with a measurement resistance, this measurement resistance thereby being arranged at an appropriate place. if the diagonal voltage of the measurement bridge is passed to a differential amplifier in the device, then the amplifier output signal is also directly influenced by the inner temperature of the device.

For the heating on both sides of a test carrier carrying a test field on its upper side, the device according to the present invention preferably has two heating and measurement devices, one of which can be pressed on from one side against the test carrier and the other from the other side of the test carrier. The heating and measurement device associated with the test field thereby preferably has an opening through which light for a reflection-photometric measurement can impinge upon the test field.

On both sides of this opening is provided the heating and measurement element and, according to the present invention, the parallel-connected additional heating resistance, already mentioned above, can be provided on the same ceramic substrate. Because of this direct heating of the test field, there is achieved an especially dependable and exact tempering of the test field.

In a further important embodiment, the heating and measurement device lying against the test carrier on the side facing away from the test field (hereinafter called the lower heating and measurement device) is arranged on a movable reception slider for the test carrier, whereby, even during the movement of the reception slider into the measurement position, heating can be carried out for the purpose of preheating the test carrier. Even in the case of moving into the measurement position, the test carrier has thereby approximately achieved the necessary temperature so that the reaction can take place practically always under the same temperature conditions.

In a particular further development, by means of the lower heating and measurement device, a preheating takes place in such a manner that, in the test field and especially in the reference field used for the evaluation, after a preselectable time, only a predetermined small temperature difference from the desired value is still present. Subsequently, in the case of applying the upper heating and measurement unit on the test field, this small temperature difference is equalised. Only a comparatively small amount of energy must hereby be passed to the test field so that the danger of an overshooting of the temperature can also be avoided in a surprisingly dependable manner. It is to be stressed that, especially in the case of test carriers constructed as test strips, as a rule, the surface of the test field with the sample to be investigated must be brought to and maintained at a definite temperature. The preheating takes place from below through the test carrier, as well as through the lower region of the test field, and it can accordingly start from a buffer action which, in practice, prevents an inadmissible exceeding of the desired temperature value. The upper heating plate, on the other hand, has a relatively small distance from the "test place" and thus from the surface of the test carrier with the sample; since only a small temperature difference has still to be overcome, by means of the upper heating plate, the desired temperature value can be approached very quickly and exactly.

Further features and advantages which are important for the present invention are given by the following embodimental examples described hereinafter, with reference to the accompanying drawings, in which.

Figure 1:
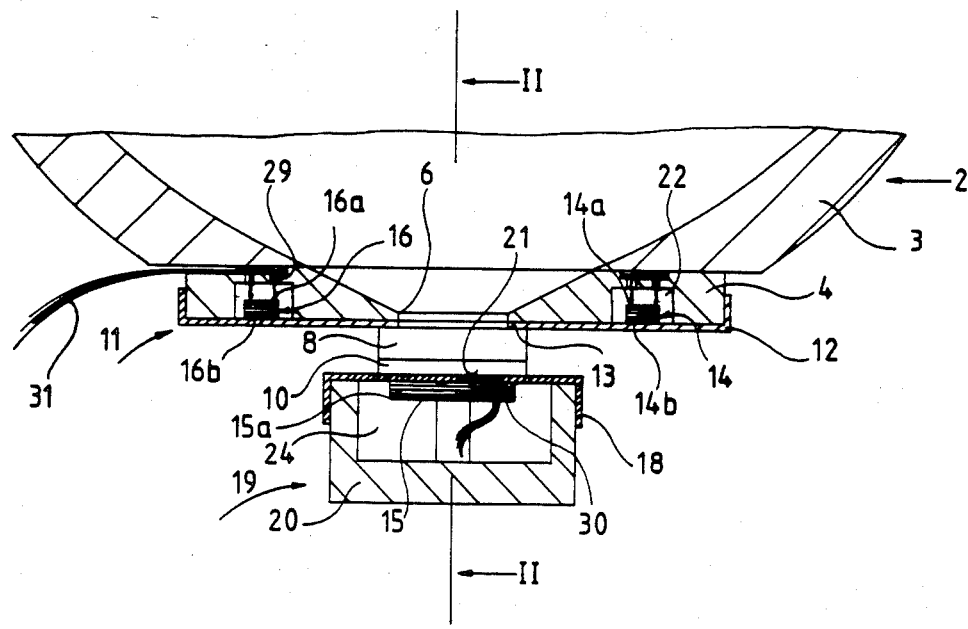
FIG. 1 is a schematic sectional illustration of a tempering device according to the present invention.

In FIG. 1, there is schematically illustrated the lower part of a measurement unit 2, this measurement unit being constructed as a well-known Ulbricht's sphere 3. Details of a construction which can, for example, be used are described in European Patent Specification No. 75766. The measurement unit 2 contains a measurement aperture plate 4 with an opening 6 through which light from the interior of the measurement unit can pass to a test field 8 of a test carrier formed as a test strip 10. The light reflected from the test field 8 is picked up by suitable means of the measurement unit 2 and evaluated in appropriate manner. The measurement aperture plate 4 is associated with a heating and measurement unit designated in toto with the reference 11. This includes two combined heating and measurement elements 14 and 16 and a metal plate 12. The heating and measurement elements 14, 16 are applied, in each case, on a ceramic platelet 14b, 16b in the form of resistance strips 14a, 16a by vapour deposition. The resistance strips are illustrated in the drawing with a highly exaggerated layer thickness. In the case of an illustration thereof in their actual layer thickness, they would not be visible in the drawing.

The measurement aperture plate 4 consists, in the illustrated embodiment, of a thermally insulating synthetic resin material upon which sits only a thin metal plate 12. However, these two constructional parts can advantageously also be produced from metal in one piece. This simplifies the production and improves the heat distribution in the then considerably thicker metal plate. In this way, their heating surface 13 is better tempered.

The heating and measurement unit 11 associated with the measurement aperture plate 4 is, in the case of the illustrated preferred embodiment, arranged above the test strip and, consequently, is referred to in the following as the upper heating and measurement unit.

From the side facing away from the test field 8 of the test strip 10, a second heating and measurement unit 19, hereinafter referred to as the lower heating and measurement unit, presses with its heating surface 21 against the rear side of the test strip 10. The heating surface 21 is a part of the surface of a metal plate 18 which is fixed to a carrier 20 made of synthetic resin for thermal insulation. The metal plate 18 carries combined heating and measurement elements 15 and 17 which, similarly to that described above for the upper heating and measurement unit 11, have resistance strips 15a and 17a which, in this case, are vapour deposited on a common ceramic platelet 30. Lead-off wires 15b, 17b serve for the electrical connection of the heating and measurement elements 15, 17. The ceramic platelets 14b, 16b and 30 are stuck on to the appropriate metal plates 12 or 18, preferably with the help of a heat-conducting adhesive which must be capable of equilibrating the stresses caused by the different coefficients of expansion of metal and ceramic.

Figure 2:
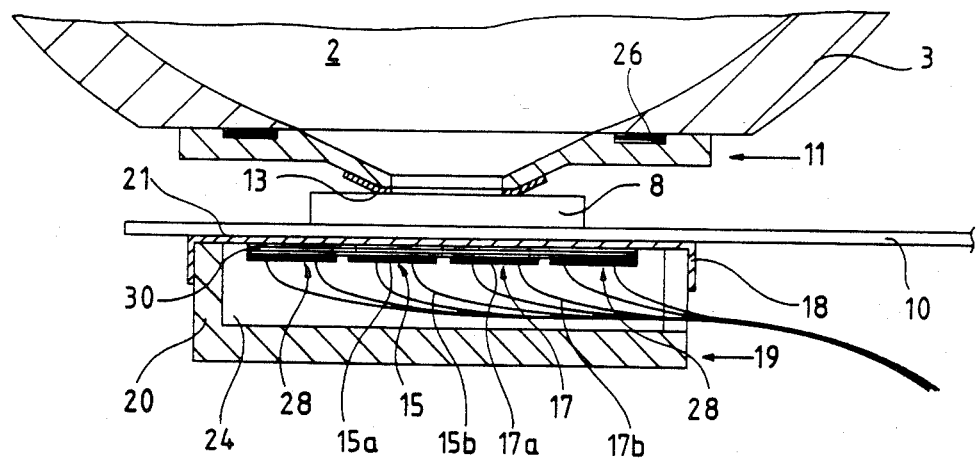
FIG. 2 is a schematic section along the line II—II of FIG. 1.

FIG. 2 shows a section along the line II—II according to FIG. 1. The test strip 10 is to be seen in its longitudinal extension. The lower metal plate 18 has, in the longitudinal direction of the test strip 10, a length which is not inconsiderably greater, at least about 1.5 times greater, than the length of the test field 8 so that the immediate vicinity of the test field 8 can be sufficiently heated. Transversely to the plane of the drawing, for the same reasons, the metal plate 18 is also constructed wider than the test strip 10 or the test field 8. In the case of the illustrated embodiment, in the plane of the drawing of FIG. 1, the ceramic platelet 30 is, for production technical reasons, somewhat narrower than the test strip 10 and its test field 8. This is not harmful because the reference surface utilised for the measurement, for which the optimum tempering must be achieved, has smaller dimensions that the test field in its totality and because the metal plate 18 also provides for a certain temperature equilibration. Furthermore, the removal of heat to the surroundings in the longitudinal direction of the test strip, which disturbs the tempering, is more markedly noticeable so that the ample dimensioning of the heating surface in the longitudinal direction illustrated in FIG. 2 is especially important.

It can be seen that, in the case of the lower heating and measurement device 19, the resistance strips 15a, 17a of the combined heating and measurement element 15, 17 are only separated from the rear side of the test strip by the, at most 2 mm. and preferably about 0.6 mm., thick plate 30 of $Al_2O_3$ ceramic and the similarly thin metal plate 18. On the other hand, the resistance strips cover almost the whole surface of the ceramic plate, preferably at least 90% thereof, in uniform thickness. Uniform thickness does not hereby necessarily mean a uniform distribution of the resistance strips on the surface. The only thing which is decisive is that the power density of the electric power to be converted into heat is almost homogeneous on the surface exactly utilised. In this way, the rear side of the test strip is, on the one hand, uniformly and homogeneously heated in the region of the reference surface utilised for the evaluation and, on the other hand, a very close coupling between the heating and measurement element and the test field is guaranteed. It is thereby important that the homogeneous heating is achieved without large masses serving for the temperature equilibration, which makes possible a rapid regulation behaviour. In the case of the illustrated construction of the lower heating and measurement unit 19, the advantages of the present invention are utilised to their full extent.

In the case of the illustrated embodiment of the upper heating and measurment unit 11, for optical and production technical reasons, it is not possible to realise a just as close proximity of the measurement element 14, 16 to the test field 8. In order to be able to realise an optically ideal shape of the Ulbricht's sphere 3, the aperture plate 4 must, on the contrary, be constructed flat in the illustrated manner. Furthermore, the opening 6 permits only a comparatively small heating surface, on which the metal plate 12 stands in contact with the surface of the test carrier 8. For production technical reasons, the heating and measurement elements 14, 16 have only relatively small surfaces (cf. FIGS. 5 and 6). These deviations from the ideal manner of construction are, in the case of the upper heating and measurement unit 11, acceptable because, as is described hereinafter with reference to FIG. 4, this is only needed for the equilibration of a relatively small temperature difference. Here, too, however, the construction according to the present invention proves to be advantageous because the compact and flat manner of construction of the heating and measurement elements 14, 16 permits a corresponding flat mode of construction of the measurement aperture plate 4 and thus an ideal shape of the Ulbricht's sphere.

Since the upper heating and measurement unit 11 displays a relatively large contact surface to the Ulbricht's sphere, for the equilibration of the conducting off of heat, a foil heating element 26 is associated with the measurement aperture 4. The foil heating element is coated on one side of its carrier foil with an appropriate heat-conductive material, especially manganin, and thus serves as a heating element. The other surface carries copper strips which form the necessary electrical connection conductor strips for the heating and measurement elements 14, 16 and for the manganin layer. Wires 29 connect the heating and measurement elements 14, 16 with the copper strips of the foil heating element and thus with the regulating unit. Hollow chambers 22 and 24 surround the heating elements 14, 16, 17, 28 in order to achieve good thermal insulation in a direction away from the heating surfaces.

Figure 3:
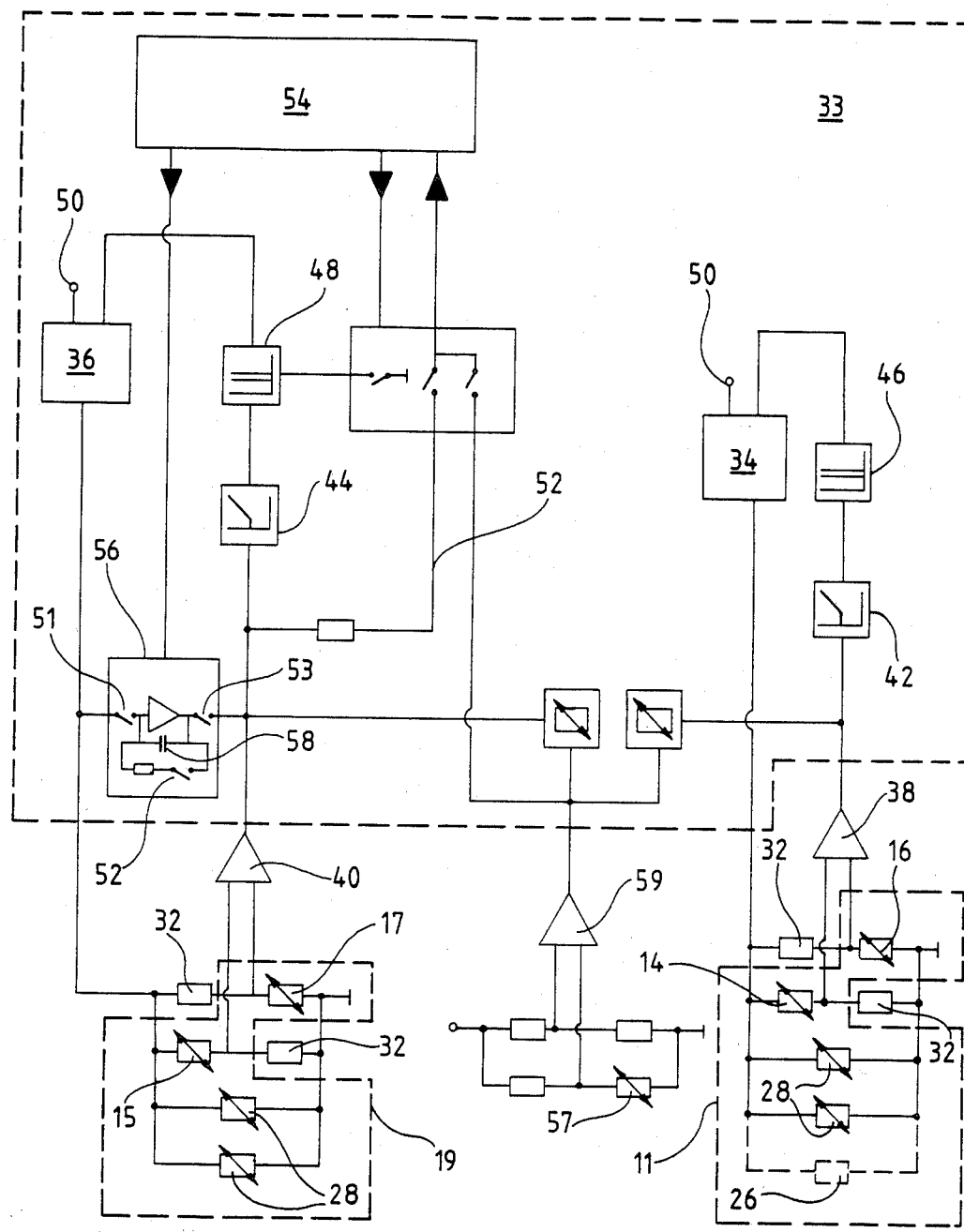
FIG. 3 is a diagram of a regulator circuit with the regulating unit and heating and measurement resistances arranged in measurement bridges.

FIG. 3 is a diagram of the circuit arrangement, on the right of which is to be seen the heating and measurement elements 14, 16 of the upper heating and measurement unit 11 and on the left of which the corresponding elements 15, 17 of the lower heating and measurement unit 19. The regulating unit is indicated in toto by 33. The said heating and measurement elements are connected with reference resistances 32 to give measurement bridges, each of which are connected to a power amplifier 34 and 36. To the bridges in question are connected in parallel heat resistances 28 for the purpose of increasing the heating ability, which are also arranged as resistance strips on the ceramic plates 14b, 16b, 30 in the manner already described. The parallel-connected heating resistances 28 could, in principle, be omitted or, however, also as required, could be separated with suitable circuit elements from the bridge or again be connected in parallel. In the case of the upper heating plate 12, the foil heating element 26 is also connected in parallel. The diagonal voltage of the measurement bridges corresponds to the actual temperature values and, via differential amplifiers 38, 40, a corresponding signal is passed to a PI regulator 42, 44 and a subsequently connected D-regulator 46, 48. The power amplifiers 34, 36 are controlled via the said regulators. The differential amplifiers 38, 40 serve for the pre-strengthening of the actual temperature value, chopper-stabilised operational amplifiers here being provided. The resistances for the amplification factor balance are to be found in a housing, together with the reference resistances 32, for good heat coupling. Such an amplifier has a very small offset, temperature coefficient and push-push. On the output of the amplifiers 38, 40, a voltage arises which is proportional to the heating plate temperature. The resistance value of the reference resistances is preferably as great as that of the heating and measurement elements 14 or 16 lying in each case on the same bridge inlet at 37° C. The output voltage of the amplifier then passes at 37° C. through 0.

As can be seen from the circuit diagram, the regulator (PI, D) is constructed in two stages, a better uncoupling of the parameters thereby being achieved. The particular parameters are specially adjusted to the properties of the upper or lower heating plate 12, 18 in order to obtain a rapid and delay-free reaction, especially in the case of laying on of a test strip. The power amplifiers 34, 36 contain an integrated voltage regulator which ensures a good suppression of variations of the feed voltage on the terminals 50. In this regulator, there is integrated an additional overload limitation. In a particular embodiment, the output voltage of the power amplifiers 34, 36 is variable within a range of 0.6 to 13 volts; still smaller voltage values are avoided in order that the regulator does not pass into the region of instability. The power amplifier 36 can possibly be separated from the regulator, the measurement bridge then being definitely supplied with a constant voltage of 0.6 volt. The circuit now serves as a temperature measurement amplifier and the actual temperature value can be introduced via a lead to a processor.

In the circuit part for the lower heating plate 18, there is provided a correction unit 56 with which, in the case of laying a test strip thereon, there is integrated the energy conducted off. The unit 56 contains an integrator which can be switched over with the help of the circuit 51, 52, 53 to the condenser discharge. The processor 54 produces a signal by means of which the integration is commenced, preferably at the start of a reception slider provided for the test strip and/or in the case of closure of a reception opening through which the test strip is laid in the apparatus or on the reception slider or the like. For this purpose, the circuit 51 is closed, whereas the circuits 52 and 53 are open. The integration is carried out for a fixed and predetermined time and, after this time, the condenser is discharged upon a signal of the processor 54 in that the circuit 51 is opened and the circuits 52 and 53 are closed. The integration condenser 58 of the correction unit 56 loses, with appropriate time constants, its charge, this discharge signal being passed to the regulators 44, 48 as correction signal. Insofar as the temperature signal is influenced at the input of the PI regulator 44, whereas the condenser discharge is influenced in the sense of an apparent lowering of the temperature, after the laying on of a test strip, the energy supplied to the heating element is very considerably increased in a corresponding manner, a rapid heating up of the test strip thereby being achieved. By means of the processor 54, the explained functional procedure is controlled. The apparatus inner temperature is determined with a measurement device containing a bridge with a measurement resistance 57 and an amplifier 59 and passed via potentiometers to the regulators and/or the processor 54.

Figure 4:
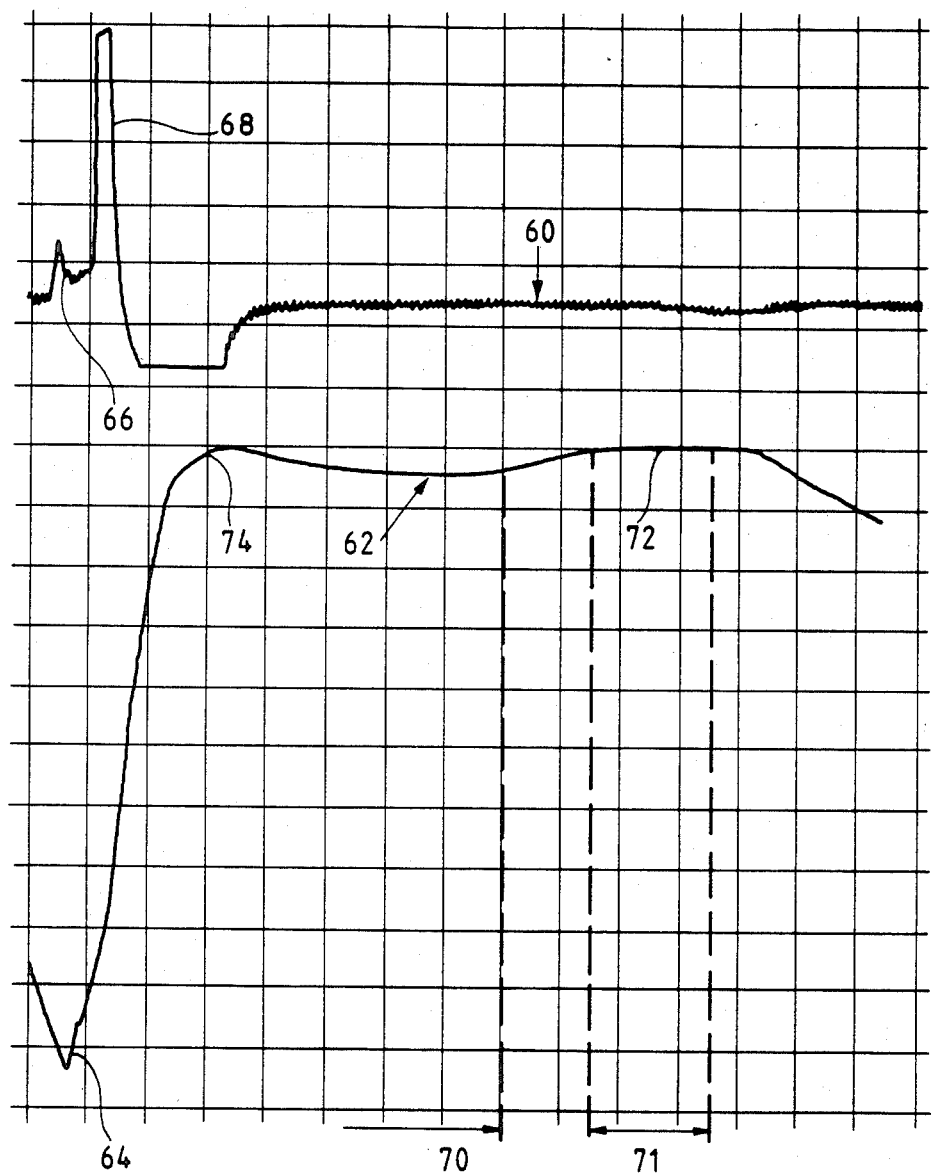
FIG. 4 shows measurement curves of the chronological course of the heating capacity, as well as of the temperature, in the measurement field.

In FIG. 4, the curve 60 shows the course of the heating capacity for the lower heating and measurement unit 19. The curve 62 represents the course of the temperature in the test field of a test strip placed in the arrangement. The temperature drops at the commencement of the course of the curve because a drop of sample has been applied. Upon laying a test strip on the lower heating plate, the temperature in the test field begins to rise (at 64). The conducting off of energy to the test strip which is, as a rule, cooler, results in an increase of the heat energy by post-regulation of the associated regulator corresponding to the peak 66 for the introduced heating capacity. The above-explained correction unit 56 determines the peak 66 by integration during a fixed period of time. After this time, the integration condenser is discharged and there follows a controlled increase of the heating power which is the greater, the lower the temperature of the test strip is at the commencement of the heating procedure. This increase is to be seen in the curve 60 at the section 68. By means of this preferred construction, it is ensured that the cool test strip is heated up very quickly, without it resulting in a substantial overshooting of the temperature (at 74). The dimensioning of the correction unit 56 is determined empirically.

Up to the point of time 70, the test strip is exclusively preheated by the lower heating plate. At this point of time, the upper heating plate of the measurement unit is also pressed on to the test field and, consequently, there takes place a certain increase of the actual temperature value, the required desired value 72 thereby being achieved and also maintained within the shortest possible time. The measurement is carried out shortly after the time point 70 in the case of a practically constant temperature course in the time interval 71. Thereafter, after lifting up the measurement unit with the upper heating plate, the temperature again drops. Because of the preheating taking place up to the time point 70, the test strip must, after pressing on of the measurement unit, only be slightly further heated, which can take place in the shortest possible time. The preheating preferably takes place in the course of the movement of the test strip on a reception slider to the measurement unit.

Figure 5:
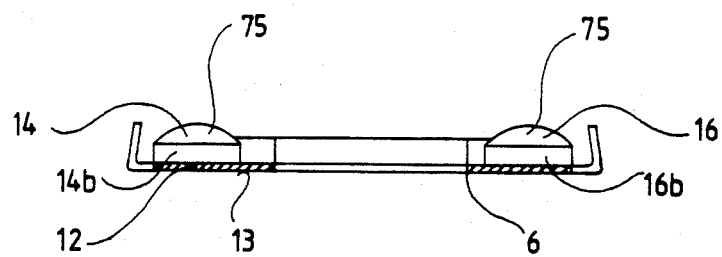
FIGS. 5 and 6 show an embodiment of an upper heating and measurement device arranged on the measurement unit, in longitudinal section and in plan view.
Figure 6:
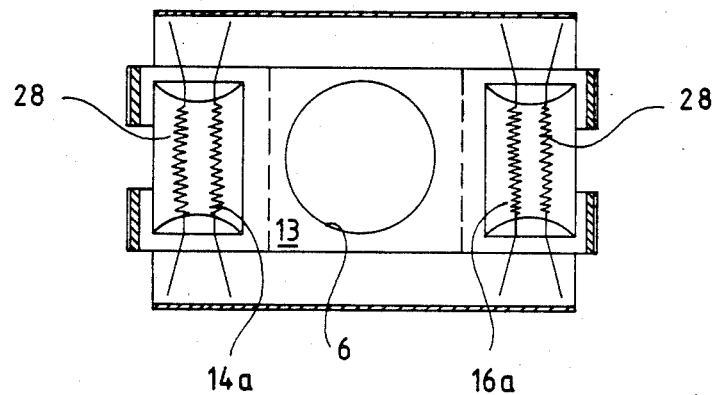

FIGS. 5 and 6 show, respectively, a section through and a view of an embodiment of the upper heating and measurement unit 11. The metal plate 12 has, in the middle, the opening 6 on both sides of which are arranged the two combined heating and measuring elements 14, 16 in the form of resistance strips 14a, 16a. In the view according to FIG. 6, for the purpose of simplicity, they are shown as simple zigzags. In actual fact, the vapour-deposited resistance strips 14b, 16a 14a, 16a preferably run in a meandering form over the surface of the substrates 14b and 16b. On the same ceramic substrate 14b, 16b, there is also present, in each case, a heating element 28 which, according to FIG. 3, is connected in parallel to the measurement bridge with the elements 14, 16. The ceramic substrates carrying the heating and measuring elements 14, 16 and also the heating element 28 are stuck on to the heating plates 12, preferably by means of a silver conductive adhesive, or soldered on in appropriate manner. In FIG. 6, there can also be seen the heating surface 13 which, because of the large opening 6, can only contact the measurement field 8 of the test strip 10 (FIGS. 1 and 2) on a comparatively small surface. In FIG. 5, there is to be seen a glass sealing 75 of the heating and measurement elements 14, 16.

Figure 7:
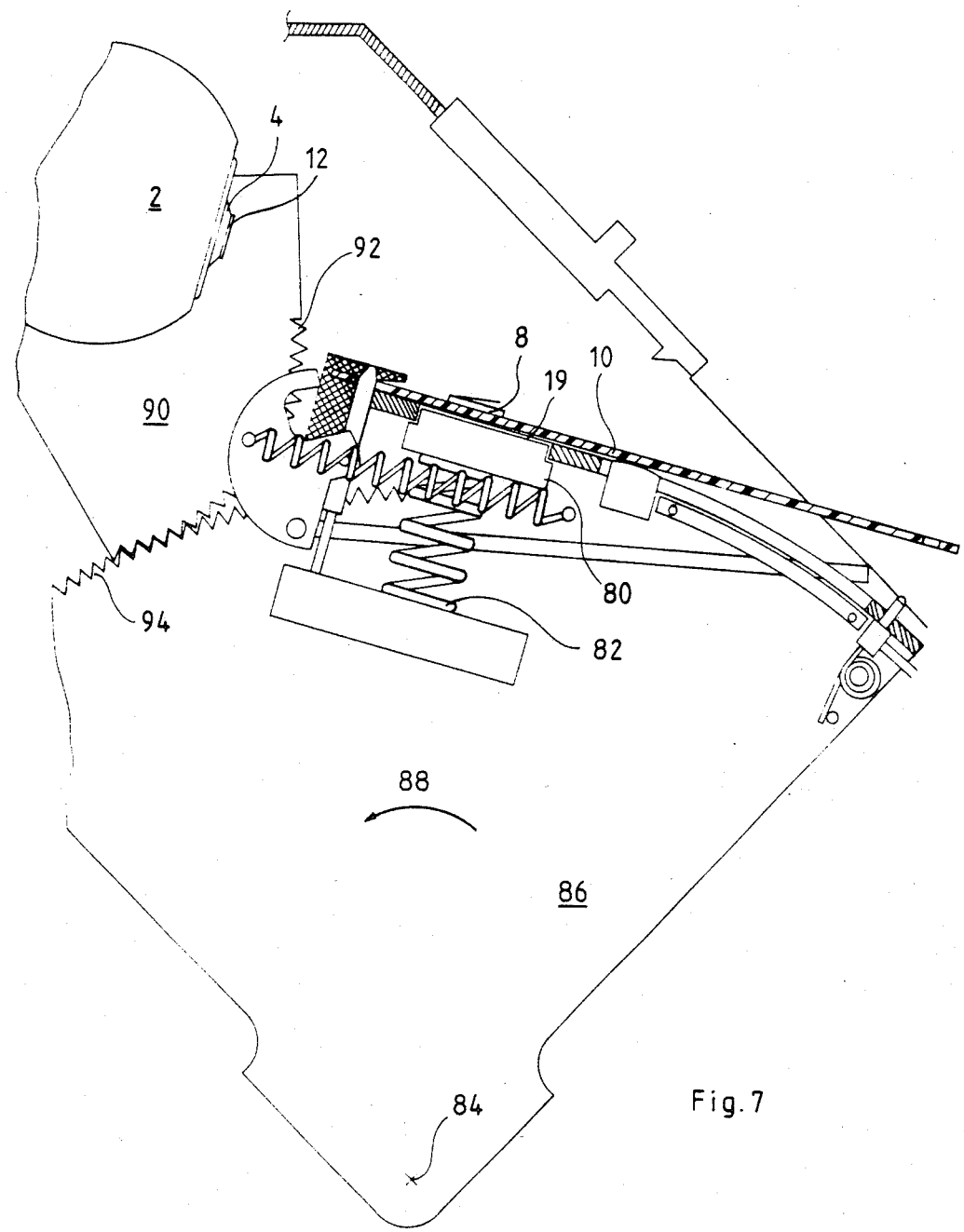
FIG. 7 is a schematic illustration of an arrangement with a reception slider for a test strip.

In FIG. 7, there is schematically illustrated an arrangement in which the lower heating and measurement unit 19 is arranged on a pressure plate 80. The pressure plate 80 is impinged against by a spring 82 and it is present on a reception slider 86 tiltable about an axis 84. The test strip 10 can be tensioned on the reception slider 86 in a manner which need not here be explained in more detail and the test field 8 can thereby be heted by means of the heating plate 18 in the manner explained hereinbefore. It is here of decisive importance that the preheating of the test field 8 already takes place during the tilting of the reception slider 86 in the direction of the arrow 88 into the measurement position. The measurement unit 2 is also arranged on a tiltable slider 90 with a toothed rim 92 which is in engagement with a toothed rim 94 on the reception slider 86. In the measurement position, the measurement shutter 4 lies with the upper heating plate 12 on the test field 8. Details thereof are to be found in Federal Republic of Germany Patent Application No. P 3321785.8 and in the corresponding commonly assigned U.S. application Ser. No. 619,016 of Dieter Meinecke, Rainer Van Rijckevorsel, Manfred Pauli, Rudolf Schüssler and Thomas Jäck entitled "Apparatus For The Evaluation Of A Test Carrier For The Analytical Determination of Components Of A Body Fluid" and filed June 11, 1984.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

We claim:

1. The combination of a test carrier having a test field and a device for the evaluation of said test carrier for the analytical determination of components of body fluids, comprising:

a test carrier having a test field; and
   a device for the evaluation of said test carrier for the analytical determination of components of body bluids comprising;
   a tempering device and a regulating unit, the tempering device including at least one heating and measurement unit, said at least one heating and measurement unit having a heating surface which can be homogeneously heated with at least one resistance heating element and which can be pressed flatly against the test carrier in the region of the test fieldutilized for the evaluation;
   at least one resistance heating element having at least one first part arranged in close proximity to the heating surface;
   said at least one first part having at least one portion thereof which serves as temperature measurement section, arranged in close proximity to the heating surface and comprising a material with a temperature-dependent electrical resistance to form at least one combined heating and temperature measuring element; and
   said at least one heating and measurement unit including a flat substrate and said at least one resistance heating element including resistance strips carried on a first surface of the substrate, the substrate comprising said heating surface, said heating surface being at least substantially as large as the test field of the test carrier used for the evaluation, the resistance strips being so dimensioned and distributed that there is obtained a uniform distribution of the electrical power density on said first substrate surface, at least a part of the resistance strips forming said at least one combined heating and temperature measuring element;
   said at least one combined heating and temperature measuring element being associated with said regulating unit so that the electrical resistance of the temperature measurement section is used for the regulation of the temperature of the heating and measurement unit by means of the regulating unit.

2. The combination according to claim 1, in which the regulating unit includes two reference resistors in a measurement bridge having a bridge diagonal and wherein in said tempering device said at least one first part of said at least one resistance heating element arranged in close proximity to the heating surface includes at least two portions which serve as temperature measurement sections which are connected to form combined heating and temperature measuring elements with the two reference resistors in the measurement bridge in such a manner that the voltage of the bridge diagonal corresponds to the actual temperature value of the heating surface.

3. The combination according to claim 1, wherein the regulating unit includes circuit means for applying increased heating power for short period of time, after the heating surface is pressed against the test carrier.

4. The combination according to claim 1, wherein the regulating unit includes a measurement device for measuring the temperature of the surroundings of the heating and measurement unit in order to introduce a correction signal corresponding to this temperature to the regulating unit.

5. The combination according to claim 1, wherein the substrate includes a heat conductive plate forming said heating surface on one side thereof and a ceramic plate of at most 2 mm. thickness positioned adjacent and extending essentially parallel to said heat conductive plate, said ceramic plate having a side lying opposite the heating surface on which said resistance strips are vapour deposited, said resistance strips being of a metal with temperature-dependent resistance.

6. The combination according to claim 5, wherein the heat conductive plate comprises a metal plate and the heating surface is located on one side of said metal plate opposite the side of the metal plate with which the side of the ceramic plate is full-facedly connected.

7. The combination according to claim 1 wherein said test carrier has a first side which carries said test field and a second side opposite said first side, wherein the tempering device includes at least two heating and measurement units, a first one of which can be pressed on from the first side carrying the test field and the second heating and measurement unit can be pressed from the second side against the test carrier, the heating and measurement unit associated with the first side having a through-opening for light and having on each of the opposite-lying sides of this opening one of said at least one combined heating and temperature measuring elements.

8. The combination according to claim 7, wherein the test carrier has lower and upper sides, said first side being said upper side and said second side being said lower side, wherein said tempering device includes a reception slider for said test carrier and wherein the second heating and measurement unit associated with the lower side of the test carrier is disposed on said reception slider for the test carrier, which reception slider is movable from a reception position into a measurement position, and wherein said second heating and measurement unit associated with the lower side of the test carrier is positioned and arranged on said reception slider so that when the test carrier is disposed ons aid reception slider said test carrier may be heated even during the movement of the reception slider into the measurement position for the pupose of preheating the test carrier so that there is present only a predetermined small temperature difference from a desired temperature value and, wherein said first heating and measurement unit is positioned and arranged adjacent the measurement position so that the test field of the test carrier can be pressed against the first heating and measurement unit when the test carrier carried by the reception slider is in the measurement position, the small temperature differences thereby being equalized.

\* \* \* \* \*

UNITED STATES PATENT AND TRADEMARK OFFICE
CERTIFICATE OF CORRECTION

PATENT NO. : 4,720,372

DATED : January 19, 1988

INVENTOR(S) : Werner Fey, et al.

It is certified that error appears in the above-identified patent and that said Letters Patent is hereby corrected as shown below:

Column 2, line 46 for "inuslatdly" read -- insulatedly --.

Column 4, line 47 for "resin)." read -- resin), --.

Column 4, line 54 for "if" read -- If --.

Column 6, line 14 for "withthe" read -- with the --.

Column 10, line 45 for "heted" read -- heated --.

Column 11, line 11 for "bluids" read -- fluids --.

Column 12, line 50 for "ons aid" read -- on said --.

Signed and Sealed this

Twenty-first Day of March, 1989

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,720,372

DATED : January 19, 1988

INVENTOR(S) : Werner Fey, et al.

It is certified that error appears in the above-identified patent and that said Letters Patent is hereby corrected as shown below:

Column 10, line 22 for "14b, 16a 14a, 16a" should read -- 14b, 16b 14a, 16a --.

Signed and Sealed this

Twenty-seventh Day of June, 1989

Attest:

DONALD J. QUIGG

Attesting Officer

Commissioner of Patents and Trademarks